US009682901B2

(12) United States Patent
Lapinski et al.

(10) Patent No.: US 9,682,901 B2
(45) Date of Patent: Jun. 20, 2017

(54) HYDROCARBON PROCESSING APPARATUSES AND PROCESSES FOR PRODUCING N-PENTANE AND ISOBUTANE

(71) Applicant: UOP LLC, Des Plaines, IL (US)

(72) Inventors: Mark Paul Lapinski, Aurora, IL (US); David Lowry, Mount Prospect, IL (US); Matthew Lippmann, Chicago, IL (US); David James Shecterle, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 67 days.

(21) Appl. No.: 14/586,409

(22) Filed: Dec. 30, 2014

(65) Prior Publication Data

US 2016/0185688 A1 Jun. 30, 2016

(51) Int. Cl.
C07C 6/10 (2006.01)
C07C 5/27 (2006.01)

(52) U.S. Cl.
CPC .............. *C07C 5/2791* (2013.01); *C07C 6/10* (2013.01); *B01J 2219/00006* (2013.01); *C07C 2521/04* (2013.01); *C07C 2523/42* (2013.01)

(58) Field of Classification Search
CPC .......................................................... C07C 6/08
USPC .................................. 585/708, 702, 706, 310
See application file for complete search history.

(56) References Cited

U.S. PATENT DOCUMENTS 3,761,535 A * 9/1973 Sieg ...................... C07C 5/2791
585/314
6,423,880 B1 * 7/2002 Randolph ................. C07C 6/10
585/310
7,902,418 B2 3/2011 Schmidt et al.

OTHER PUBLICATIONS

U.S. Appl. No. 14/267,737, filed May 1, 2014.
U.S. Appl. No. 14/267,742, filed May 1, 2014.
U.S. Appl. No. 14/267,745, filed May 1, 2014.
U.S. Appl. No. 14/267,838, filed May 1, 2014.
U.S. Appl. No. 14/267,845, filed May 1, 2014.
U.S. Appl. No. 61/987,348, filed May 1, 2014.
U.S. Appl. No. 61/994,583, filed May 16, 2014.
U.S. Appl. No. 14/446,591, filed Jul. 30, 2014.
PCT application No. PCT/US14/49878 filed Aug. 6, 2014.

* cited by examiner

*Primary Examiner* — Sharon Pregler

(57) ABSTRACT

Hydrocarbon processing apparatuses and processes for producing n-pentane and isobutane are provided herein. In an embodiment, a process for producing n-pentane and isobutane includes providing a hydrocarbon feed stream that includes C4 and C5 hydrocarbons. A recycle stream that includes C4+ hydrocarbons and the hydrocarbon feed stream is combined to produce a combined feed stream. The combined feed stream is separated to produce an iC4 product stream, an nC5+ product stream, and an iC5/nC4 feed stream. The iC5/nC4 feed stream is simultaneously disproportionated and isomerized in an isomerization zone to produce an intermediate stream that includes C3-C6 hydrocarbons. The C3-C6 hydrocarbons in the intermediate stream are separated to produce a C3− stream and the recycle stream that includes C4+ hydrocarbons.

14 Claims, 1 Drawing Sheet

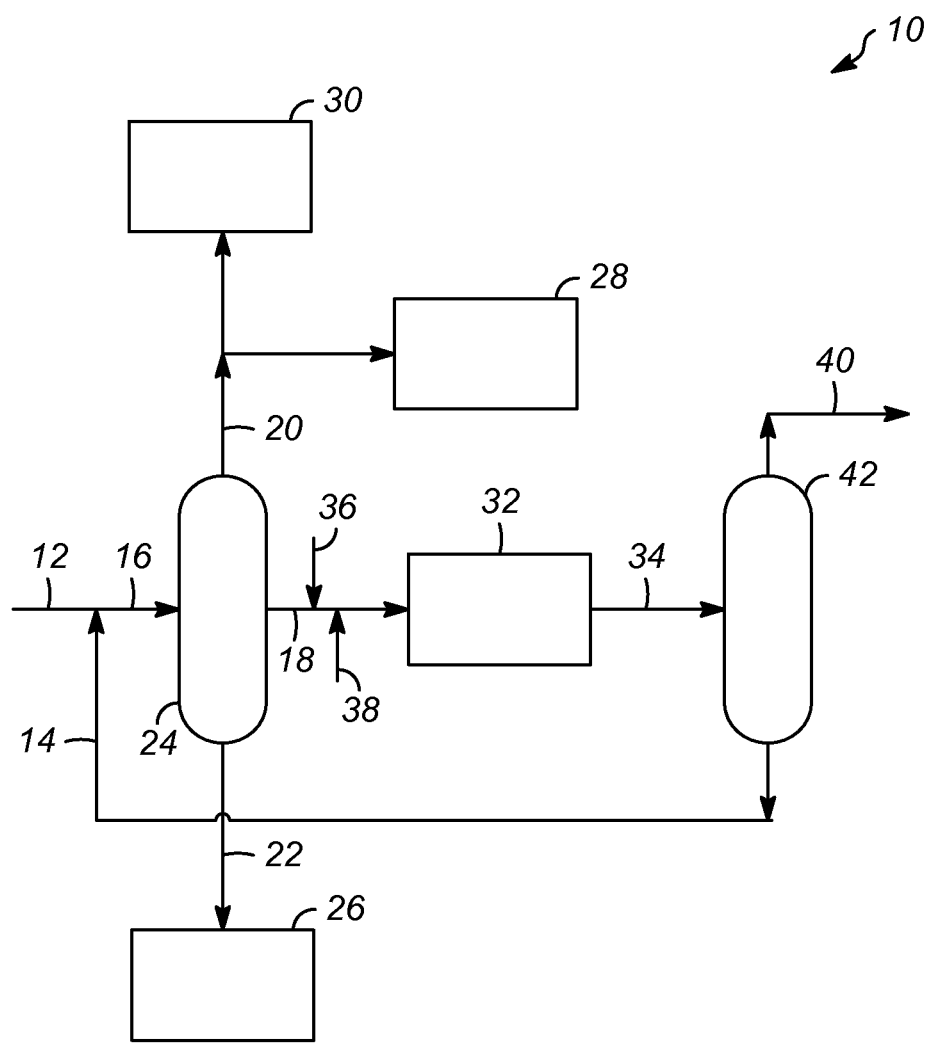

HYDROCARBON PROCESSING APPARATUSES AND PROCESSES FOR PRODUCING N-PENTANE AND ISOBUTANE

TECHNICAL FIELD

The technical field generally relates to hydrocarbon processing apparatuses and processes for producing n-pentane and isobutane, and more particularly relates to hydrocarbon processing apparatuses and processes for producing n-pentane from isopentane and isobutane from n-butane.

BACKGROUND

Petroleum refiners often produce hydrocarbon products, such as turbine fuel, diesel fuel, middle distillates, and gasoline boiling hydrocarbons among others, by hydroprocessing a hydrocarbon stream derived from crude oil or fractions thereof. Hydrocarbon streams that are often subjected to hydroprocessing include vacuum gas oils, heavy gas oils, and other hydrocarbon streams recovered from crude oil by distillation. Conventional hydroprocessing techniques can include, for example, hydrocracking, hydrotreating, hydroisomerization, hydrodesulfurization, and the like. Gasoline boiling hydrocarbons and middle distillates, in particular, are often produced by hydrotreating the hydrocarbon stream, such as vacuum gas oil, to reduce nitrogen and sulfur content of the hydrocarbon stream followed by catalytically hydrocracking the hydrocarbon stream into product hydrocarbons of lower average molecular weight and boiling point. Hydrocracking is conducted under appropriate conditions, including elevated temperature and elevated pressure in the presence of hydrogen, to produce a naphtha stream that includes C4 and C5 isomers, as well as higher boiling hydrocarbons.

Various products can be obtained or derived from the naphtha stream, including components included in gasoline products such as C5+ hydrocarbons as well as C4− hydrocarbons that have other industrial uses. N-butanes present in the naphtha stream are generally separated from the naphtha stream and isomerized to produce isobutane, which is useful as a feed to an alkylation stage to make alkylates or as feed to a dehydrogenation stage to make isobutylene. C5+ hydrocarbons are generally separated from the naphtha stream and fed to a gasoline blending stage for producing gasoline.

Gasoline products generally benefit from elevated octane values and, as such, various isomerized hydrocarbons are generally desired for the gasoline products. However, ethanol is often included in gasoline products and has a higher octane value than many other species present in the gasoline products, thereby reducing the need for other higher octane species in the gasoline products. However, Reid Vapor Pressure (RVP) of the gasoline product is another factor that restricts the components included in the gasoline products.

Isopentane is often a desirable component in gasoline products due to relatively high octane values thereof. However, isopentane has a vapor pressure of about 77 kPa at 20° C., and it would be desirable to include components with lower vapor pressure in the gasoline products to minimize the RVP of the gasoline products. N-pentane has a lower vapor pressure than isopentane, and gasoline products with higher overall C5 hydrocarbon content can be obtained by decreasing isopentane content and increasing n-pentane content while still meeting RVP specifications. Decreased octane values resulting from lower isopentane content in the gasoline products is offset by the ethanol content of the gasoline products. Isopentane content in the gasoline products can be decreased by converting at least some of the isopentane from the naphtha stream into other hydrocarbon species. However, it is undesirable to add additional operating units into existing hydrocarbon processing apparatuses for purposes of converting isopentane and increasing n-pentane yield from the naphtha stream.

Accordingly, it is desirable to provide hydrocarbon processing apparatuses and processes for producing n-pentane and isobutane including conversion of isopentane from the naphtha stream. Further, it is desirable to provide hydrocarbon processing apparatuses and processes that enable conversion of isopentane but that do not require additional operating units. Furthermore, other desirable features and characteristics will become apparent from the subsequent detailed description and the appended claims, taken in conjunction with the accompanying drawings and this background.

BRIEF SUMMARY

Hydrocarbon processing apparatuses and processes for producing n-pentane and isobutane are provided herein. In an embodiment, a process for producing n-pentane and isobutane includes providing a hydrocarbon feed stream that includes C4 and C5 hydrocarbons. A recycle stream that includes C4+ hydrocarbons and the hydrocarbon feed stream is combined to produce a combined feed stream. The combined feed stream is separated to produce an iC4 product stream, an nC5+ product stream, and an iC5/nC4 feed stream. The iC5/nC4 feed stream is simultaneously disproportionated and isomerized in an isomerization zone to produce an intermediate stream that includes C3-C6 hydrocarbons. The C3-C6 hydrocarbons in the intermediate stream are separated to produce a C3− stream and the recycle stream that includes C4+ hydrocarbons.

In another embodiment, a process for isomerizing an iC5/nC4 feed stream includes providing a hydrocarbon feed stream that includes C4 and C5 hydrocarbons. A C4+ stream that includes isobutane and the hydrocarbon feed stream are combined to produce a combined feed stream. N-butane and isopentane are removed from the combined feed stream to produce the iC5/nC4 feed stream. The n-butane and isopentane are removed from the combined feed stream after combining the C4+ stream and the hydrocarbon feed stream in the absence of an intermediate reaction of components in the combined feed stream prior to removing the n-butane and isopentane therefrom. The iC5/nC4 feed stream is simultaneously disproportionated and isomerized to produce an intermediate stream that includes C3-C6 hydrocarbons.

In another embodiment, a hydrocarbon processing apparatus includes a first fractionation column, an isomerization zone, and a second fractionation column. The first fractionation column has the capacity to receive a combined feed stream that includes C4+ hydrocarbons, and the first fractionation column further has the capacity to separate the combined feed stream into an iC4 product stream, an nC5+ product stream, and an iC5/nC4 feed stream. The isomerization zone is in fluid communication with the first fractionation column for receiving the iC5/nC4 feed stream. The isomerization zone has the capacity to isomerize and disproportionate the iC5/nC4 feed stream in the presence of an isomerization catalyst to produce an intermediate stream that includes C3-C6 hydrocarbons. The second fractionation column is in fluid communication with the isomerization zone for receiving the intermediate stream. The second fractionation column has the capacity to separate the intermediate stream into a C3− stream and a recycle stream that includes C4+ hydrocarbons.

BRIEF DESCRIPTION OF THE DRAWINGS

The various embodiments will hereinafter be described in conjunction with the following drawing figures, wherein like numerals denote like elements, and wherein:

FIGURE is a schematic diagram of a hydrocarbon processing apparatus and process for producing n-pentane and isobutane in accordance with an exemplary embodiment

DETAILED DESCRIPTION

The following detailed description is merely exemplary in nature and is not intended to limit the hydrocarbon processing apparatuses and processes for producing n-pentane and isobutane. Furthermore, there is no intention to be bound by any theory presented in the preceding background or the following detailed description.

Hydrocarbon processing apparatuses and processes for producing n-pentane and isobutane are provided herein that include simultaneously disproportionating and isomerizing an iC5/nC4 feed stream in an isomerization zone to produce isobutane and n-pentane. As referred to herein, "CX" means hydrocarbon molecules that have "X" number of carbon atoms, CX+ means hydrocarbon molecules that have "X" and/or more than "X" number of carbon atoms, and CX− means hydrocarbon molecules that have "X" and/or fewer than "X" number of carbon atoms. As also referred to herein, "iC" refers to an iso-paraffin and "nC" refers to a normal paraffin. As also referred to herein, a "iC5/nC4" stream, or similar designations pertaining to various streams, means that the stream includes the referenced hydrocarbons present as a majority of all hydrocarbons present therein. Thus, the iC5/nC4 feed stream contains at least 50 weight % of isopentane and n-butane, based on the total weight of the iC5/nC4 feed stream.

It has been found that, in isomerization zones that are conventionally employed to isomerize n-butane into isobutane during hydrocarbon processing, disproportionation reactions also occur and yield from isomerization and disproportionation reactions can be controlled based upon the various reaction conditions in the isomerization zone. For example, isopentane is disproportionated to produce isobutane and isohexane, and isobutane is disproportionated to produce propane and isopentane. Isobutane and isopentane are simultaneous isomerized to produce their corresponding normals. By providing the iC5/nC4 feed stream as opposed to a straight nC4 stream, simultaneous disproportionation and isomerization of n-butane and isopentane can occur thereby enabling n-pentane and isobutane to be produced without adding additional operating units to the hydrocarbon processing apparatus, and the n-pentane and isobutane can be recovered. Further, by simultaneously disproportionating and isomerizing the iC5/nC4 feed stream, yields of n-pentane and isobutane may be increased as compared to straight isomerization of n-butane because disproportionation generally yields more product per pass than isomerization. Disproportionation and isomerization of the isopentane also decreases isopentane content of gasoline products that would otherwise include the isopentane, and n-pentane produced by the simultaneous disproportionation and isomerization of the iC5/nC4 feed stream can be included in the gasoline products.

An exemplary embodiment of a process for producing n-pentane and isobutane will now be described with reference to an exemplary hydrocarbon processing apparatus 10 as shown in the FIGURE. In accordance with the exemplary method, a hydrocarbon feed stream 12 is provided that includes C4 and C5 hydrocarbons. In embodiments, the hydrocarbon feed stream 12 is a hydrotreated naphtha stream that is recovered from crude oil by distillation. By "hydrotreated", it is meant that the naphtha stream or a precursor thereof is hydrotreated to reduce nitrogen and sulfur content thereof. The hydrotreated naphtha stream may be obtained by distillation of a fraction from the crude oil, such as a vacuum gas oil fraction, hydrotreating the vacuum gas oil fraction, and catalytically hydrocracking the hydrotreated gas oil fraction through conventional techniques. Hydrocracking may be conducted under appropriate conditions, including elevated temperature and elevated pressure in the presence of hydrogen, to produce the hydrotreated naphtha stream that includes C4 and C5 hydrocarbons, i.e., n-butane and n-pentane as well as isobutane and isopentane. Higher boiling hydrocarbons may also be present in the hydrotreated naphtha stream, and the hydrotreated naphtha stream may generally contain C4 to C12 hydrocarbons.

Referring to the FIGURE, a C4+ stream 14 that includes isobutane is combined with the hydrocarbon feed stream 12 to produce a combined feed stream 16. It is to be appreciated that the C4+ stream 14 includes any stream that contains C4+ species that are to be separated, and the C4+ stream 14 may be provided from any source. The C4+ stream 14 is substantially free of C3− species, and the C4+ stream 14 may be obtained by fractionation with residual C3− species present therein due to practical separation inefficiencies associated with conventional fractionation techniques for separation of C3− species from C4+ species.

In an embodiment, the C4+ stream 14 is a recycle stream 14 that includes C4+ hydrocarbons, and the recycle stream 14 may be obtained by separation of an isomerized intermediate stream 34 as described in further detail below. Because isomerization and disproportionation do not result in complete conversion of the n-butane and isopentane, recycle of unconverted species to be combined with the hydrocarbon feed stream 12 may maximize overall conversion rates. Further, because a range of C4+ hydrocarbons are produced during isomerization and disproportionation, including species that are also present in the hydrocarbon feed stream 12, combining the recycle stream 14 and the hydrocarbon feed stream 12 enables efficient separation of the hydrocarbon species from both the recycle stream 14 and the hydrocarbon feed stream 12 as described in further detail below.

N-butane and isopentane are removed from the combined feed stream 16 to produce an iC5/nC4 feed stream 18. In embodiments, the n-butane and isopentane are removed from the combined feed stream 16 after combining the C4+ stream 14 and the hydrocarbon feed stream 12 in the absence of any intermediate reactions of components in the combined feed stream 16 prior to removing the n-butane and isopentane therefrom, i.e., the combined feed stream 16 is subject to separation directly after combining the hydrocarbon feed stream 12 and the C4+ stream 14. Referring to the FIGURE, in embodiments, the combined feed stream 16 is separated to produce an iC4 product stream 20, an nC5+ product stream 22, and the iC5/nC4 feed stream 18. For example, the hydrocarbon processing apparatus 10 may include a first fractionation column 24 that has the capacity to receive the combined feed stream 16 and to separate the combined feed stream 16 into the iC4+ product stream 20, the nC5+ product stream 22, and the iC5/nC4 feed stream 18, and the combined feed stream 16 may be fed to the first fractionation column 24 after combining the C4+ stream 14 and the hydrocarbon feed stream 12 in the absence of intermediate reaction stages. Separating the combined feed stream 16 through fractionation in the first fractionation column 24 may be conducted in accordance with conventional techniques including the use of a divided wall fractionation column, with the iC5/nC4 feed stream 18 taken as a side draw from the first fractionation column 24, the iC4 product stream 20 taken as an overhead vapor stream, and the nC5+ product stream 22 taken as a bottom liquid stream from the first fractionation column 24. In embodiments, the nC5+ product stream 22 is provided to a gasoline blending stage 26 for incorporation into a gasoline product. In other embodiments and although not shown, the nC5+ product stream 22 may be returned for further fractionation, such as in a main distillate fractionation column (not shown), to further separate the hydrocarbon species contained therein. The iC4 product stream 20 may be provided to one or more further processing stages. For example, in embodiments, the iC4 product stream 20 may be provided to an alkylation stage 28 and/or a dehydrogenation stage 30 where isobutane contained in the iC4 product stream 20 is employed in accordance with conventional techniques.

The iC5/nC4 feed stream 18 is simultaneously disproportionated and isomerized in an isomerization zone 32 to produce an intermediate stream 34 that includes C3-C6 hydrocarbons. Isopentane is disproportionated to produce isobutane and isohexane, and isobutane is disproportionated to produce propane and isopentane. Isobutane and isopentane are simultaneous isomerized to produce their corresponding normals. Simultaneous disproportionation and isomerization of the iC5/nC4 feed stream 18 and product yields may depend upon a variety of variables including, but not limited to, isomerization catalyst used, content of the iC5/nC4 feed stream 18 including the presence of hydrogen, water, or species in the iC5/nC4 feed stream 18 that inhibit disproportionation; reaction temperature; and liquid hourly space velocity of the iC5/nC4 feed stream 18. Disproportionation does not always occur in conventional isomerization zones, and the aforementioned variables may be controlled, as described in further detail below, to vary disproportionation and isomerization reactions in the isomerization zone 32 and shift yield of n-pentane and isobutane products.

In embodiments and referring to the FIGURE, the hydrocarbon processing apparatus 10 includes the isomerization zone 32 in fluid communication with the first fractionation column 24 for receiving the iC5/nC4 feed stream 18. The isomerization zone 32 has the capacity to isomerize and disproportionate the iC5/nC4 feed stream 18 in the presence of an isomerization catalyst to produce the intermediate stream 34. To effectuate isomerization and disproportionation of the iC5/nC4 feed stream 18 in the isomerization zone 32, the iC5/nC4 feed stream 18 may be contacted with the isomerization catalyst using the catalyst in a fixed-bed system, a moving-bed system, a fluidized-bed system, or in a batch-type operation. The iC5/nC4 feed stream 18 may be contacted with the isomerization catalysts, which may be in particulate form, in upward, downward, or radial-flow fashion. The iC5/nC4 feed stream 18 may be in the liquid phase, a mixed liquid-vapor phase, or a vapor phase when contacted with the isomerization catalyst particles. The isomerization zone 32 may be in a single reactor or in two or more separate reactors with suitable connections therebetween to insure that a desired isomerization temperature is maintained at the entrance to each reactor. Two or more reactors in sequence may enable improved isomerization and disproportionation through control of individual reactor temperatures and for partial catalyst replacement without a process shutdown.

Various conventional isomerization catalysts may be employed in the isomerization zone 32, although use of particular isomerization catalysts may be dependent upon content of the iC5/nC4 feed stream 18. For example, in various embodiments, suitable conventional isomerization catalysts include, but are not limited to, halogenated alumina, sulfated zirconia, tungstated zirconia, or zeolite-containing isomerization catalysts. The isomerization catalyst may be amorphous, e.g. based upon amorphous alumina, or zeolitic. The sulfated zirconia isomerization catalyst and halogenated alumina may further include platinum. Another suitable conventional isomerization catalyst includes a tungstated support of an oxide or hydroxide of a Group IVB (IUPAC 4) metal, such as zirconium oxide or hydroxide, at least a first component which is a lanthanide element and/or yttrium component, and at least a second component being a platinum-group metal component. Conventional isomerization operating conditions and techniques may be employed based upon the particular isomerization catalyst employed.

Some isomerization catalysts are more effective than others to effectuate disproportionation in addition to isomerization. In embodiments, the isomerization catalyst includes halogenated alumina, such as chlorided alumina, which has been found to be particularly effective for disproportionation and isomerization of isopentane and n-butane in the iC5/nC4 feed stream 18. Conventional halogenated alumina isomerization catalysts may be employed, and the halogenated alumina catalysts generally contain less than about 80 weight % aluminum halide, such as less than about 10 weight % aluminum halide, based upon the total weight of the halogenated alumina catalysts. When halogenated alumina is employed as the isomerization catalyst, the iC5/nC4 feed stream 18 is simultaneously disproportionated and isomerized substantially in the absence of water (typically at less than about 0.05 wppm $H_2O$) and also substantially in the absence of oxygenated compounds which can be converted into water by the catalyst in the isomerization zone 32 (typically less than about 0.1 wppm of the oxygenated compounds). Additionally, simultaneous disproportionation and isomerization of the iC5/nC4 feed stream 18 using the halogenated alumina is conducted in the presence of hydrogen ($H_2$). In embodiments, hydrogen is admixed with the iC5/nC4 feed stream 18 through a hydrogen stream 36. The hydrogen stream 36 is substantially free of water (typically at less than about 0.1 vppm). In embodiments, to maintain low water levels to the isomerization zone 32, the iC5/nC4 feed stream 18 and the hydrogen stream 36 are each passed through adsorbent beds prior to mixing. The adsorbent beds are designed to remove water, oxygenated compounds and sulfur compounds.

Isomerization and disproportionation conditions in the isomerization zone 32 include reactor temperatures that may range from about 40° C. to 250° C. Reactor operating pressures may range from about 100 kPa to 10 MPa absolute, such as from about 0.5 and about 4 MPa absolute. Liquid hourly space velocities may range from about 0.2 to about 25 volumes of iC5/nC4 feed stream 18 per hour per volume of isomerization catalyst, such as a range of from about 0.5 to about 15 $h^{-1}$. Additionally, depending upon the isomerization catalyst employed, hydrogen is admixed with the iC5/nC4 stream 18 and provides a mole ratio of hydrogen to iC5/nC4 feed stream 18 of from about 0.01 to about 20. A hydrogen to hydrocarbon ratio may be monitored in the intermediate stream 34 that is produced by simultaneously disproportionating and isomerizing the iC5/nC4 feed stream 18. The hydrogen to hydrocarbon ratio may be maintained within a desired range to provide for the presence of excess hydrogen during disproportionation and isomerization.

In embodiments, the iC5/nC4 feed stream 18 further includes a disproportionation inhibitor, which may be admixed with the iC5/nC4 feed stream 18 through an inhibitor feed stream 38. In particular, further the disproportionation inhibitor from the inhibitor feed stream 38 and the iC5/nC4 feed stream 18 may be combined after producing the iC5/nC4 feed stream 18. Admixing the disproportionation inhibitor with the iC5/nC4 feed stream 18 may be conducted to control disproportionation reactions in the isomerization zone 32 by passivating a surface of the isomerization catalyst, thereby shifting product yield as desired. Examples of suitable disproportionation inhibitors consist of cyclic and/or paraffin hydrocarbons chosen from cyclopentane, methylcyclopentane, cyclohexane, benzene, C7+ paraffins, C7+ cyclic hydrocarbons, and combinations thereof. In embodiments, the disproportionation inhibitor is present in amounts of less than or equal to about 50 weight %, such as from about 0.05 to about 10 weight %, based on the total weight of the combined iC5/nC4 feed stream 18 and inhibitor stream 38. In embodiments using a halogenated alumina catalyst in the isomerization zone 32, the inhibitor stream 38 is substantially free of water (typically at less than about 0.05 wppm $H_2O$) and includes less than about 0.1 wppm oxygenated compounds. In embodiments, the iC5/nC4 feed stream 18 and inhibitor stream 38 are combined and then passed through an adsorbent bed to remove water, oxygenated compounds and sulfur. In other embodiments, the disproportionation inhibitor is absent from the iC5/nC4 feed stream 18.

In embodiments, reaction conditions in the isomerization zone 32 are dynamic and are controlled to affect yield of isobutane and n-pentane in the intermediate stream 34. For example, in embodiments, the iC5/nC4 feed stream 18 is simultaneously disproportionated and isomerized at a first set of operating variables including temperature, liquid hourly space velocity, and disproportionation inhibitor content of the iC5/nC4 feed stream 18 to produce a first yield of n-pentane and isobutane. During operation of the hydrocarbon processing apparatus 10, one or more of the temperature, liquid hourly space velocity, or disproportionation inhibitor content of the iC5/nC4 feed stream 18 is adjusted from the first set of operating variables to produce a second yield of n-pentane and isobutane different from the first yield. For example, increasing the liquid hourly space velocity and/or including disproportionation inhibitor in the iC5/nC4 feed stream 18 results in retardation of disproportionation in the isomerization zone 32 and enables a reduction in isobutane content and an increase n-pentane content in the intermediate stream 34 as compared to the first yield produced at the first set of operating variables. Additionally, lower temperatures also retard disproportionation in the isomerization zone 32 and lead to a reduction in isobutane content and an increase n-pentane content in the intermediate stream 34. In embodiments, the intermediate stream 34 includes isobutane in an amount of from about 10 to about 50 weight %, such as from about 15 to about 45 weight %, or such as from about 20 to about 40 weight %, based on the total weight of the intermediate stream 34. In embodiments, the intermediate stream 34 includes n-pentane in an amount of from about 3 to about 10 weight %, such as from about 7 to about 10 weight %, based on the total weight of the intermediate stream 34.

C3-C6 hydrocarbons in the intermediate stream 34 are separated to produce a C3– stream 40 and the recycle stream 14 that includes C4+ hydrocarbons. In embodiments and referring to the FIGURE, the hydrocarbon processing apparatus 10 includes a second fractionation column 42 in fluid communication with the isomerization zone 32 for receiving the intermediate stream 34. The second fractionation column 42 has the capacity to separate the intermediate stream 34 into the C3– stream 40 and the recycle stream 14 through conventional fractionation techniques. In embodiments, the second fractionation column 42 is in fluid communication with the first fractionation column 24 to provide the recycle stream 14 to the first fractionation column 24 as a portion of the combined feed stream 16.

The following Examples are intended to illustrate the processes for producing n-pentane and isobutane as described herein, and are not to be viewed as limiting.

EXAMPLES

Trial runs of simultaneous disproportionation and isomerization of a hydrocarbon feed stream were conducted using a kinetic model simulation process to determine yield of n-pentane and isobutane under various process conditions. In the simulations, a chlorided-alumina catalyst containing platinum was used as the isomerization catalyst and the following process conditions within the isomerization zone were employed: 450 psig, 0.15 $H_2$/hydrocarbon mole ratio at the outlet of the isomerization zone, either 1 or 6 $h^{-1}$ LHSV, and an average catalyst bed temperature of 330° F. (165.6° C.). Hydrocarbon Feed A consisted of 60 wt % n-butane and about 40 wt % isopentane. Hydrocarbon Feed B consisted of 2.0 wt % cyclohexane (CH), 59 wt % n-butane and 39 wt % isopentane and represents the addition of a small stream of disproportionation inhibitor to the isomerization zone. It is to be appreciated that other disproportionation inhibitors may be employed as an alternative to CH, such as benzene, methylcyclopentane, cyclopentane, $C_7+$ paraffins, $C_7+$ cyclic hydrocarbons, and combinations or mixtures thereof. Product yields at various reaction conditions for Hydrocarbon Feed A and Hydrocarbon Feed B are shown below in TABLE I.

TABLE I

|  | iC5/nC4 Feed Stream A | | iC5/nC4 Feed Stream B | |
| --- | --- | --- | --- | --- |
| Example | 1 | 2 | 3 | 4 |
| Pressure, MPa | 3.1 | 3.1 | 3.1 | 3.1 |
| LHSV, $h^{-1}$ | 1 | 6 | 1 | 6 |
| Avg Temperature, ° C. | 165.5 | 165.5 | 165.5 | 165.5 |
| Intermediate Stream Content, wt % | | | | |
| H2, wt % | 0.5 | 0.5 | 0.5 | 0.5 |
| C1 | 0.9 | 0 | 0.2 | 0 |
| C2 | 2.4 | 0.1 | 0.4 | 0 |
| C3 | 3 | 0.3 | 1.1 | 0.2 |
| iC4 | 44 | 22.2 | 37.4 | 15.4 |
| nC4 | 29.4 | 41.2 | 25.7 | 43.9 |
| iC5 | 9.4 | 23.3 | 22.5 | 28.5 |
| nC5 | 3.1 | 7.9 | 7.4 | 9.2 |
| iC6 | 6.6 | 3.8 | 3.5 | 0.5 |
| nC6 | 0.9 | 0.6 | 0.5 | 0.1 |

TABLE I-continued

|  | iC5/nC4 Feed Stream A | | iC5/nC4 Feed Stream B | |
| --- | --- | --- | --- | --- |
| Example | 1 | 2 | 3 | 4 |
| CP, MCP, Bz | 0 | 0 | 0.1 | 0.8 |
| CH | 0 | 0 | 0.1 | 0.6 |
| C7+ | 0 | 0.2 | 0.7 | 0.3 |
| Sum | 100 | 100 | 100 | 100 |
| Conv., Selectivities | | | | |
| nC4 conversion, % | 51.0 | 31.3 | 56.4 | 25.6 |
| iC5 conversion, % | 76.6 | 41.6 | 42.4 | 26.9 |
| iC4 selectivity, % | 71.8 | 62.6 | 75.0 | 60.1 |
| C6 paraffin sel., % | 12.2 | 12.4 | 8.0 | 2.3 |

Examples 1 to 4 demonstrate that the product yields can be altered to favor a desired product via the use of process conditions and/or the addition of disproportionation inhibitor. Example 2 in TABLE I illustrates the impact of shifting LHSV from 1 h$^{-1}$ to 6 h$^{-1}$ LHSV between Examples 1 and 2. As can be seen from TABLE I, n-butane is isomerized to isobutane (forward isomerization) at a lesser yield in Example 2 as compared to Example 1, while isopentane is isomerized to n-pentane (reverse isomerization) at a greater yield in Example 2 as compared to Example 1. A small amount of propane is made (0.3 wt %) in Example 2, showing that the disproportionation (DP) reaction of $2iC_4 \rightarrow C_3 + iC_5$ was a minor reaction pathway in Example 2. The production of $C_6$ paraffins shows the isopentane disproportionation reaction pathway in Examples 1 and 2, but the extent of this reaction was reduced in Example 2 as compared to Example 1. In Example 1, the forward $C_4$ and reverse $C_5$ isomerization reactions occur with greater product yield and disproportionation yields more $C_3$ and $C_6$ paraffin hydrocarbons as compared to Example 2. Example 1 also shows higher selectivity to isobutane at comparable $C_6$ paraffin selectivity as compared to Example 2.

Comparison of Examples 3 and 4 indicates the inhibition effects due to the addition of 2.0 wt % cyclohexane as a disproportionation inhibitor in the iC5/nC4 feed streams. Comparing Example 3 to Example 1 shows that the isobutane and $C_6$ paraffin yields declined due to a significant decline in the isopentane conversion from reduced disproportionation reactions. The n-pentane yield increased, showing that the isomerization activity is less impacted by the presence of the disproportionation inhibitor. Similar effects can be seen between Examples 4 and 2.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration in any way. Rather, the foregoing detailed description will provide those skilled in the art with a convenient road map for implementing an exemplary embodiment. It being understood that various changes may be made in the function and arrangement of elements described in an exemplary embodiment without departing from the scope as set forth in the appended claims.

What is claimed is:

1. A process for producing n-pentane and isobutane, wherein the process comprises:
providing a hydrocarbon feed stream comprising C4 and C5 hydrocarbons;
combining a recycle stream comprising C4+ hydrocarbons and the hydrocarbon feed stream to produce a combined feed stream;
separating the combined feed stream to produce an iC4 product stream, an nC5+ product stream, and an iC5/nC4 feed stream;
simultaneously disproportionating and isomerizing the iC5/nC4 feed stream in an isomerization zone substantially in the absence of water and in the presence of hydrogen to produce an intermediate stream comprising C3-C6 hydrocarbons; and
separating the C3-C6 hydrocarbons in the intermediate stream to produce a C3− stream and the recycle stream comprising C4+ hydrocarbons.

2. The process of claim 1, further comprising maintaining a hydrogen to hydrocarbon ratio in the intermediate stream produced by simultaneously disproportionating and isomerizing the iC5/nC4 feed stream.

3. The process of claim 1, wherein simultaneously disproportionating and isomerizing the iC5/nC4 feed stream comprises simultaneously disproportionating and isomerizing the iC5/nC4 feed stream at a first set of operating variables comprising temperature, liquid hourly space velocity, and disproportionation inhibitor content of the iC5/nC4 feed stream to produce a first yield of n-pentane and isobutane.

4. The process of claim 3, further comprising adjusting one or more of the temperature, liquid hourly space velocity, or disproportionation inhibitor content of the iC5/nC4 feed stream from the first set of operating variables to produce a second yield of n-pentane and isobutane different from the first yield.

5. The process of claim 4, wherein adjusting the one or more of the temperature, liquid hourly space velocity, or cyclics content comprises increasing the liquid hourly space velocity and/or including disproportionation inhibitor in the iC5/nC4 feed stream to reduce the isobutane content and increase n-pentane content in the second yield as compared to the first yield produced at the first set of operating variables.

6. The process of claim 1, wherein simultaneously disproportionating and isomerizing the iC5/nC4 feed stream comprises simultaneously disproportionating and isomerizing the iC5/nC4 feed stream comprising a disproportionation inhibitor.

7. The process of claim 6, wherein the disproportionation inhibitor consists of cyclic and/or paraffin hydrocarbons chosen from cyclopentane, methylcyclopentane, cyclohexane, benzene, C7+ paraffins, C7+ cyclic hydrocarbons, and combinations thereof, and wherein simultaneously disproportionating and isomerizing the iC5/nC4 feed stream comprises simultaneously disproportionating and isomerizing the iC5/nC4 feed stream comprising the disproportionation inhibitor.

8. The process of claim 6, further comprising combining the disproportionation inhibitor and the iC5/nC4 feed stream after producing the iC5/nC4 feed stream.

9. The process of claim 1, wherein providing the hydrocarbon feed stream comprises providing a hydrotreated naphtha stream comprising C4 and C5 hydrocarbons.

10. The process of claim 1, wherein separating the combined feed stream comprises fractionating the combined feed stream to produce the iC4 product stream, the nC5+ product stream, and the iC5/nC4 feed stream.

11. The process of claim 1, wherein separating the combined feed stream comprises separating the combined feed stream after combining the recycle stream and the hydrocarbon feed stream in the absence of intermediate reaction stages.

12. The process of claim 1, further comprising providing the nC5+ product stream to a gasoline blending stage.

13. The process of claim 1, further comprising providing the iC4 product stream to an alkylation stage and/or a dehydrogenation stage.

14. A process for isomerizing an iC5/nC4 feed stream, wherein the process comprises:
   providing a hydrocarbon feed stream comprising C4 and C5 hydrocarbons;
   combining a C4+ stream comprising isobutane and the hydrocarbon feed stream to produce a combined feed stream;
   removing n-butane and isopentane from the combined feed stream to produce the iC5/nC4 feed stream, wherein the n-butane and isopentane are removed from the combined feed stream after combining the C4+ stream and the hydrocarbon feed stream in the absence of an intermediate reaction of components in the combined feed stream prior to removing the n-butane and isopentane therefrom; and
   simultaneously disproportionating and isomerizing the iC5/nC4 feed stream to produce an intermediate stream comprising C3-C6 hydrocarbons.

* * * * *